Figure 1:
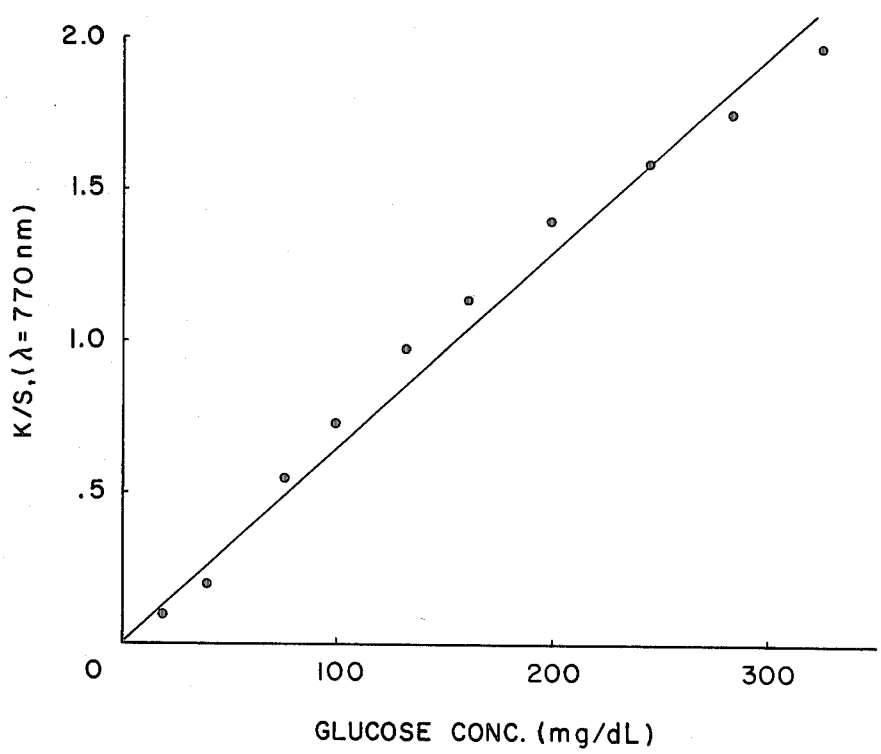

United States Patent [19]

Chen

[11] Patent Number: 4,543,338

[45] Date of Patent: Sep. 24, 1985

[54] WIPE-OFF TEST DEVICE

[75] Inventor: Shuenn-tzong Chen, Irvine, Calif.

[73] Assignee: Miles Laboratories, Inc., Elkhart, Ind.

[21] Appl. No.: 500,976

[22] Filed: Jun. 3, 1983

[51] Int. Cl.$^4$ .................... G01N 33/52; G01N 21/78
[52] U.S. Cl. ..................... 436/170; 422/56; 427/2; 435/14; 435/805
[58] Field of Search .......... 436/169, 95, 170; 422/56, 57; 435/28, 805, 14; 427/2

[56] References Cited

U.S. PATENT DOCUMENTS

| | | | |
|---|---|---|---|
| 3,092,465 | 6/1963 | Adams, Jr. et al. | 422/56 |
| 3,298,789 | 1/1967 | Mast | 436/95 X |
| 3,630,957 | 12/1971 | Rey et al. | 422/56 X |
| 4,015,462 | 4/1977 | Greyson et al. | 436/166 X |
| 4,278,439 | 7/1981 | White | 436/66 |
| 4,301,115 | 11/1981 | Rapkin et al. | 422/56 |

*Primary Examiner*—Arnold Turk
*Attorney, Agent, or Firm*—Roger N. Coe

[57] ABSTRACT

A test device for determining the presence of a substance in a test sample is disclosed, as well as methods for making and using it. The device comprises a support member having a reagent layer affixed to it which contains a reagent system which produces a detectable response in the presence of the analyte. The reagent layer has an upper layer affixed to the side opposite the support member. The upper layer comprises a polymer which is at least partially crosslinked.

The method of use comprises contacting the device with the test sample, wiping the upper layer free of test sample residue, and observing a detectable response.

9 Claims, 1 Drawing Figure

WIPE-OFF TEST DEVICE

1. INTRODUCTION

The present invention relates to a test device for measuring an analyte in a test sample, whereby the sample is contacted with the device and excess sample is subsequently wiped off. Following wiping, a detectable response is observed in the device if the particular analyte is present in the sample.

The invention has usefulness in many areas of analysis. Measurement of glucose in blood or serum has long been a concern of prime importance to the diabetic. Measurement of the potassium level in blood aids the physician in the diagnosis of conditions leading to muscle irritability and excitatory changes in myocardial infarction. Such conditions include oliguria, anuria, urinary obstruction and renal failure due to shock. The detection of occult blood in feces is likewise of considerable help in the diagnosis of many internal pathologies.

With test samples such as blood and feces, a test device in which the sample is physically applied, followed by direct visual or instrumental observation, has an attendant difficulty not experienced with aqueous solutions, such as urine. Both blood and feces contain highly pigmented components which can interfere with observation of a detectable response attributable to the presence of particular substance under analysis.

Needless to say, a quick facile method for determining such test sample constituents, whereby excess sample can be merely wiped off, would greatly enhance the state of these technologies, as well as any others where rapid, accurate determinations would be beneficial.

2. BACKGROUND OF THE INVENTION

The use of a test device in which a carrier matrix, such as paper, is impregnated with an indicator for glucose is described in U.S. Pat. No. 2,981,606. Such a device is said to be useful in determining glucose in blood.

The '606 patent teaches a glucose indicator comprising a mixture of glucose oxidase, peroxidase and a color-forming substance such a benzidine or o-tolidine. By impregnating paper with such a composition and drying, a test paper is obtained which can be used to measure glucose by contacting it with a drop of blood or urine and observing any color formed.

But the device of the '606 patent has a significant drawback where blood is the intended test sample: the colored matter in blood interferes with easy observation of the color produced by a positive test. This problem was addressed by the patentees of U.S. Pat. Nos. 3,092,465 and 3,298,789. Both of these patents deal with various aspects of a test device for testing for glucose in blood. Both describe test devices having an enzyme system in a porous carrier matrix such as in the '606 patent.

This impregnated composite is protected from the staining propensity of hemoglobin and other blood components through use of a protective coating, or upper layer, of a membrane permeable to water and glucose, but which screens out relatively large molecules. Thus, interfering pigments such as hemoglobin can be washed off prior to observing the device for the appearance of, or change in, color attributable to the presence of glucose. The protective membrane can be cast as a liquid film, for example a solution of cellulose acetate in benzene, which is allowed to dry thereby leaving a continuous, porous film over the reagent-impregnated paper layer.

Similar technology is disclosed in U.S. Pat. No. 3,992,158. This disclosure is directed broadly to an integral test element having at least two layers and comprising a spreading layer and a reagent layer. A liquid sample is contacted with the spreading layer, which is porous and which causes the test sample to spread out over the surface of the spreading layer.

To summarize the background of technological developments leading up to the present invention, devices are known which detect the presence of many analytes present in liquid test samples. For example, glucose in blood can be detected using a paper strip impregnated with glucose oxidase, peroxidase and an appropriate indicator.

Such a device, while having enjoyed marked commercial success in glucose urinalysis, nevertheless has a serious drawback in blood analysis: interference with observing color formation attributable to such blood components as hemoglobin. The '465, '789 and '158 patents addressed this problem by providing a porous film overlay to filter out the interfering blood components, while permitting the aqueous portion of the sample to permeate the film, and to contact the reagent layer.

Such devices permit removal of the interfering components by washing in a stream of water. However, a wipe-off technique has for all practical purposes eluded prior experimenters. The present invention affords the user the convenience of merely wiping off excess sample from the test device thereby eliminating the necessity of washing.

3. DEFINITIONS

Certain terms used in the present discussion should at this point be mentioned. Thus, the following definitions are provided to clarify the scope of the present invention, and to enable its formulation and use.

3.1 The term "substance" is used to denote water soluble components of blood, feces or other test sample, which the present invention can be used to detect. For example, substance can include glucose, hydrogen ion (pH), uric acid, cholesterol and amino acids.

3.2 By "carrier matrix" is intended a physical means for containing a reagent system capable of detecting the substance, and for permitting separation and easy removal of non-water soluble blood components. The carrier matrix comprises at least two layers: an upper layer which is porous to, and permits the passage of, water and dissolved substances through the upper layer; and a lower layer which contains the reagent system.

3.3 The "support member" contemplated includes a wide range of materials and sizes. It is ideally a relatively thin film which is elongated, having substantially flat upper and lower sides. The carrier matrix is affixed to one end of the upper side, the other end serving as a handle. Typical of materials suitable for the support member include a myriad of plastics or polymers such as cellulose acetate, polyethylene terephthalate, polycarbonates and polystyrene.

3.4 A "reagent system", as the expression is intended herein, comprises one or more ingredients which, acting singly or in concert, is capable of producing a detectable response in the presence of the particular substance under analysis. For example, such a reagent system useful for detection of glucose in blood could comprise glucose oxidase, peroxidase and an indicator which changes color in the presence of hydrogen peroxide. In addition, the reagent system can comprise any of several known pH indicators. The latter could be used in a test for blood pH. Numerous other reagent systems are usable in the present invention, the selection of which is within the ken of a person skilled in the art, given the present disclosure.

3.5 A "detectable response" is a physical or chemical manifestation or change which results from the presence of the particular substance in the test sample. It can be a change in or the appearance of color, fluorescence, luminescence, light absorption or reflectance, ultraviolet or infrared spectra and any other property which can be observed visually or instrumentally.

3.6 By "polymer" is meant a material substantially composed of protein or carbohydrate, thus containing high molecular weight chains of amino acids, glucoside, and the like. Included by the term polymer are gelatin, alginic acid and its salts, and agarose.

4. SUMMARY OF THE INVENTION

The present invention resides in the discovery of a new test device for detecting the presence of a substance in blood. It comprises an improvement in prior devices which contain a reagent system layer attached on one of its sides to a support member, the other side having affixed to it an upper layer porous to water and the substance, but which is substantially impermeable to proteins and colored pigments, such as hemoglobin, contained in blood. The improvement resides in the use, as the upper layer, of at least partially crosslinked polymers, including gelatin, alginic acid and its salts, and agarose. The improved test device enables the user to apply blood or other test sample to the upper layer, wait a predetermined time to permit the substance to pass through the upper layer to the reagent system layer, and merely wipe off the excess sample. Thus, the necessity of carefully washing off excess blood or other test sample, and the attendant interfering proteinaceous matter and colored pigments, is precluded. By having the capability of being wiped off, the test device provides improved observability of the detectable response, greater accuracy and convenience, and minimizes the occurrence of false negative results.

5. ELEMENTS OF THE TEST DEVICE

The present test device comprises four basic elements: a support member, a lower reagent system layer, a reagent system and an upper layer. The reagent system layer contains the reagent system responsive to the substance to be analyzed, and has the upper layer affixed to one side, the other side being affixed to the support member.

5.1 The Support Member

The composite upper and lower layers (hereafter, the carrier matrix) is affixed to one end of an elongated support member such that the lower layer of the matrix is situated between the upper layer and support member. In use, the other end of the support member serves as a convenient handle. Such a test device can be held at the handle end, while the other end bearing the carrier matrix is contacted with the test sample.

Useful materials for the support member include films of a myriad of plastics or polymers. Examples include such polymeric materials as cellulose acetate, polyethylene terephthalate, polycarbonates and polystyrene. The support can be opaque or it can transmit light or other energy. Preferred supports include transparent materials capable of transmitting electromagnetic radiation of a wavelength in the range of about 200 nanometers (nm) to 900 nm. The support need not, of course, transmit over the entire 200–900 nm region, although for fluorometric detection of analytical results it is desirable that the support be transparent over a band wider than, or at least equal to, the absorption and emission spectra of any fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics.

The carrier matrix is preferably affixed to an elongated support member having an upper, substantially flat face, such as an oblong piece of polystyrene film. The carrier matrix is affixed to the flat face at one end, leaving the other end of the polystyrene to serve as a convenient handle.

The carrier matrix can be affixed to the support member by any means compatible with the intended use. One method is to use a double faced adhesive tape between the carrier matrix and the support member. One such tape is known as Double Stick ®, available from 3M Company. Another way to affix the test means is to cast a film of an emulsion of an aqueous polymer phase (i.e., a hydrophilic carrier matrix) containing the reagent system directly onto the support, followed by a drying step.

5.2 The Reagent System

As stated, supra, the reagent system employed depends on the ultimate analysis to be performed with the test device. If the substance to be analyzed is glucose, the reagent system is any one of many known formulations which produce a colorimetric or other detectable response to that sugar. A preferred reagent system for glucose comprises glucose oxidase, peroxidase and a redox indicator such as benzidine and/or its derivatives. Redox indicators suitable for such a glucose-sensitive reagent system include o-tolidene, 3,3',5,5'-tetramethylbenzidine (TMB) guaiac, o-dianisidine, 4-aminoantipyrene and others known in the art. They are capable of being oxidized, in the presence of hydrogen peroxide and a peroxidatively active substance, to produce a colored product.

Other reagent systems usable in the invention include those capable of detecting uric acid, cholesterol and amino acids. For uric acid, a suitable reagent system could comprise uricase, peroxidase and a redox indicator; for cholesterol, it could comprise cholesterol oxidase, peroxidase and a redox indicator; and for amino acids, the respective amino acid oxidase, peroxidase and a redox indicator.

The invention can also be used for detecting fecal occult blood, and a suitable reagent system for that use could comprise an organic hydroperoxide and a redox indicator.

5.3 The Reagent Layer

The reagent system is contained in a layer of the carrier matrix situated between the upper layer and the support member. In addition to a reagent system the reagent layer can also include other layers which are complementary to the reagent system, and assist in the use of the test device. For instance, it may be desirable to include a light reflecting layer to aid in light reflectance measurements, or an absorptive layer to aid in absorption of the test sample from the upper layer.

A preferred reagent layer comprises filter paper or other bibulous material which has been incorporated with the ingredients of the reagent system, such as glucose oxidase, peroxidase and TMB. The filter paper can be impregnated with the reagent system by dipping it into a solution containing the reagent system ingredients. If necessary, two or more dip solutions can be employed, such that the filter paper is successively dipped in each with drying between dippings. Such a multiple dip procedure enables the isolation of reagent system ingredients which are incompatible with one another in solution, but which are compatible in the dry state.

Following impregnation, the dried filter paper can be coated with the upper layer to form a composite carrier matrix and then mounted on the support member, or it can be mounted directly to the support member followed by application of the upper layer. Alternatively, other layers can be affixed to the filter paper, such as light reflective and/or absorptive layers, followed by application of the upper layer and affixing the carrier to the support member.

Although many means of affixing the carrier matrix to the support member will be apparent to those skilled in the art, it is preferred to use a double faced adhesive tape such as Double Stick (3M Company).

5.4 The Upper Layer

The unique upper layer of the present invention comprises a protein or carbohydrate polymer which has been hardened by crosslinking. The resultant crosslinked polymer has been found to be uniquely resistant to coloring due to blood components. Whereas the film coverings mentioned in Section 2, supra, can be used in a washing procedure, attempts to wipe off excess sample result in at least partial embedding of the colorant in the film and/or damage to the surface of the film. The hardened polymer of the present invention does not suffer from such a shortcoming. Thus, the test device described and claimed herein is used merely by applying test sample to the matrix and wiping if off, such as with a napkin, cotton ball or paper towel. Any response to the analyte is then observed unimpeded by interfering sample components.

The upper layer is preferably applied to the reagent layer directly as a solution or emulsion. Thus polymer, an appropriate crosslinking agent and possibly other ingredients are taken up in a suitable solvent such as water and cast as a film onto the reagent layer. Subsequent drying produces a carrier matrix capable of detecting a sample component, while trapping interfering sample components at the surface of the upper layer. Moreover such interferants can be wiped off the surface of the upper layer leaving the crosslinked polymer film virtually intact.

Crosslinking of the polymer used in the upper layer can be achieved by any known crosslinking method, whether chemical (through any of several crosslinking agents) or by the use of high energy radiation, such as high intensity ultra violet light. Typical chemical crosslinking agents include polyfunctional aziridine compounds such as XAMA 7 (a proprietary composition manufactured by Cordova Chemical Co. of North Muskegon, MI) and glutaraldehyde, and it is the use of such compounds which is a preferred route to the desired hardening of the upper layer.

The degree of crosslinking necessary to achieve the hardened polymer upper layer can vary over a wide range, and the experimenter can easily tailor the appropriate extent of crosslinking to the particular intended assay for which the ultimate test device is to be used. Thus, besides the specific degrees of crosslinking achieved in the Examples, infra, any extent of crosslinking is within the scope of the present invention, provided it be sufficient to provide a hardened upper layer which remains intact after wiping off excess sample, such as with a paper tissue or towel. Of course, the degree of crosslinking should not be such as to preclude permeation of the aqueous components of the test sample through the upper layer to the reagent system layer. It is also anticipated that too much crosslinking may result in crosslinked polymers which are brittle and/or difficult to apply or affix to the reagent layer.

6. EXAMPLES

The following Examples are provided to further assist in making and using the present invention. Preferred embodiments are described in experimental detail and the results analyzed. The Examples are meant to be illustrative and enabling only, and are in no way intended as limiting the scope of the invention described and claimed herein.

6.1 Preparation of a Wipe-Off Test Device for Glucose in Blood

Experiments were performed to prepare a test strip device for measuring glucose in whole blood. Laboratory filter paper was impregnated with glucose oxidase, peroxidase and TMB, followed by drying. An aqueous solution of gelatin and crosslinking agent was coated onto one side of the dried filter paper and permitted to dry. The coated paper was then mounted, paper side down, onto a polystyrene strip.

A strip of filter paper (Whatman 3MM) was dipped into a solution containing 1.5% (w/v) TMB.2HCl, and 1.0% (wv) Gantrez AN-139 in water and dried at 60° C. Gantrez AN is an interpolymer of methyl vinyl ether and maleic anhydride, and is marketed by GAF Corp. The dried paper was then immersed in a second solution containing 4.8% (w/v) polyvinyl pyrrolidone, 5.2% (w/v) tris(hydroxymethyl) aminomethane, 2.2% (w/v) malonic acid, 3.7% (w/v) disodium malonate, $4 \times 10^6$ IU/L peroxidase and 56,000 IU/L glucose oxidase in distilled water. Following drying at 60° C., the paper was immersed in a third solution containing 1.5% (w/v) ethyl cellulose in a solvent which is 5% (v/v) ethanol and 95% (v/v) toluene, followed by drying at 60° C.

The glucose paper thus prepared produces a blue color when contacted with an aqueous solution containing glucose.

A coating solution was prepared containing 12.5% (w/v) gelatin (Type A, 275 Bloom, Fisher Scientific Co.), 0.1% (w/v) sodium benzoate, 0.5% (w/w) XAMA-7 (a proprietary crosslinking composition based on aziridine, manufactured by Cordova Chemical Co.) in water.

Glucose paper prepared as above was coated with the coating solution using a #46 Mayer rod (wet film thickness of 4.1 mils). The film was dried in an air oven at about 40° C.

The carrier matrix thus produced was then cut to a strip 0.2 inches wide and mounted at the edge of a strip of polystyrene film using a double-faced adhesive tape known as Double Stick (3M Co.). One face of the adhesive tape was applied to the uncoated side of the impregnated filter paper strip. The other side of the adhesive tape was applied to the polystyrene film.

The polystyrene film with the carrier matrix attached was then slit perpendicular to the axis of the paper strip. The resultant test devices measured 0.2 by 3.25 inches. On each, a 0.2 inch square of the carrier matrix was affixed to one end.

6.2 Evaluation of the Glucose-measuring Capability of the Test Device

An evaluation of the test device of Example 6.1 was performed. The purpose of the evaluation was to assess the capability of the device to measure glucose using a wipe-off technique.

Test devices were inoculated with whole blood samples which had been contrived to various glucose concentrations. For each sample, a drop of whole blood was applied to a reagent strip and then wiped off thirty seconds later with a cotton ball. The reacted reagent strip was examined with a SERALYZER® reflectance photometer (available from the Ames Division of Miles Laboratories, Inc.) at 770 mm twenty seconds after sample removal. This procedure was repeated using blood samples of ten different glucose concentrations.

The resultant data is recorded in the table below and is portrayed graphically in FIG. I.

| Glucose (mg/dL) | K/S (at 770 nm) |
|---|---|
| 20 | .105 |
| 41 | .218 |
| 75 | .548 |
| 101 | .735 |
| 132 | .976 |
| 161 | 1.146 |
| 200 | 1.406 |
| 245 | 1.603 |
| 282 | 1.759 |
| 325 | 1.973 |

(K/S) is defined as $$(K/S) = (1-R)^2/2R$$

in which R is the fraction of reflectance from the test device, K is a constant, and S is the light scattering coefficient of the particular reflecting medium. The above equation is a simplified form of the well-known Kubelka-Munk equation (See Gustav Kortüm, "Reflectance Spectroscopy", pp. 106–111, Springer Verlag, New York (1969).

The data shows a linear dose/response curve, indicating good performance.

What is claimed is:

1. A test device for determining the presence of a substance in a test sample comprising a carrier matrix having an upper and lower layer, the lower layer being affixed to a support member; in which the upper layer is porous to water, but impermeable to proteins and colored pigment contained in the test sample, and the lower layer comprises a reagent system capable of producing a detectable response in the presence of the substance; the improvement wherein the upper layer consists essentially of a partially crosslinked polymer of gelatin, agarose, alginic acid, a salt of alginic acid, or mixtures thereof.

2. The test device of claim 1 in which the polymer is gelatin.

3. The test device of claim 1 in which the reagent system is one capable of producing a detectable response to glucose, hydrogen ion, sodium, potassium, lithium, uric acid, cholesterol or an amino acid.

4. A method for determining the presence of a substance in a test sample, the method comprising the steps of contacting the test device of claim 1 with a test sample, thereafter wiping the upper layer free of test sample residue, and observing a detectable response.

5. A test device for determining the presence of a substance in a test sample, the device comprising:

a carrier matrix having a upper layer and a reagent system layer affixed to the upper layer, the reagent system layer comprising a bibulous material incorporated with a reagent system capable of producing a detectable response in the presence of the substance and the upper layer comprising a continuous film of a partially crosslinked polymer of gelatin, agarose, alginic acid, a salt of alginic acid, or mixtures thereof; and a support member having the reagent system layer of the carrier matrix affixed thereto.

6. The test device of claim 5 in which the reagent system comprises glucose oxidase, peroxidase, and a redox indicator.

7. The test device of claim 6 in which the indicator is 3,3',5,5'-tetramethylbenzidine.

8. A method for preparing a test device for determining the presence of a substance in a test sample, the method comprising the steps of:

incorporating a bibulous material with a reagent system to form a reagent system layer having an upper and lower side;

coating the upper side of the reagent system layer with an aqueous solution of a polymer of gelatin, agarose, alginic acid, a salt of alginic acid, or mixtures thereof, and a crosslinking agent therefor, to form a partially crosslinked upper layer and;

affixing the lower side of the reagent system layer to a support member.

9. The method of claim 8 the upper side of the reagent system layer is coated with the upper layer before the lower side of the reagent layer is affixed to the support member.

* * * * *